United States Patent
Song

(10) Patent No.: US 10,307,458 B2
(45) Date of Patent: Jun. 4, 2019

(54) PEPTIDE AS ABSORPTION ENHANCER AND COMPOSITION CONTAINING SAME

(71) Applicant: SOONCHUNHYANG UNIVERSITY INDUSTRY ACADEMY COOPERATION FOUNDATION, Chungcheongnam-do (KR)

(72) Inventor: Keon-Hyoung Song, Chungcheongnam-do (KR)

(73) Assignee: Soonchunhyang University Industry Academy Cooperation Foundation, Asan-si, Chungcheongnam-do (KR)

( * ) Notice: Subject to any disclaimer, the term of this patent is extended or adjusted under 35 U.S.C. 154(b) by 0 days.

(21) Appl. No.: 15/323,055

(22) PCT Filed: May 27, 2015

(86) PCT No.: PCT/KR2015/005308
§ 371 (c)(1),
(2) Date: Dec. 29, 2016

(87) PCT Pub. No.: WO2016/003073
PCT Pub. Date: Jan. 7, 2016

(65) Prior Publication Data
US 2017/0143785 A1  May 25, 2017

(30) Foreign Application Priority Data
Jun. 30, 2014 (KR) ........................ 10-2014-0080608

(51) Int. Cl.
*A61K 38/08* (2019.01)
*A61K 9/00* (2006.01)
*C07K 7/06* (2006.01)

(52) U.S. Cl.
CPC ............ *A61K 38/08* (2013.01); *A61K 9/0043* (2013.01); *C07K 7/06* (2013.01)

(58) Field of Classification Search
CPC ........ A61K 38/08; A61K 9/0043; A61K 9/00; C07K 7/06
USPC ................................. 530/300, 329; 514/21.8
See application file for complete search history.

(56) References Cited

U.S. PATENT DOCUMENTS

| 4,966,848 | A | * | 10/1990 | Smith | .................. | C12N 9/1029 435/193 |
| 5,223,421 | A | * | 6/1993 | Smith | .................. | C12N 9/1029 435/193 |
| 5,837,218 | A | * | 11/1998 | Peers | .................. | A61K 51/088 424/1.65 |
| 7,294,689 | B2 | * | 11/2007 | Fasano | .................. | C07K 14/28 530/328 |
| 8,557,763 | B2 | * | 10/2013 | Tamiz | .................. | C07K 7/06 514/1.1 |
| 2005/0059593 | A1 | * | 3/2005 | Fasano | .................. | C07K 14/28 424/130.1 |
| 2007/0196272 | A1 | | 8/2007 | Eddington et al. | | |
| 2008/0159984 | A1 | | 7/2008 | Ben-Sasson | | |
| 2009/0252672 | A1 | | 10/2009 | Eddington et al. | | |
| 2011/0142881 | A1 | | 6/2011 | Sasardic et al. | | |
| 2012/0027720 | A1 | | 2/2012 | Tamiz et al. | | |
| 2012/0129762 | A1 | | 5/2012 | Sato et al. | | |

FOREIGN PATENT DOCUMENTS

| KR | 10-2007-0044805 A | 4/2007 |
| KR | 10-2012-0052274 A | 5/2012 |
| WO | 2007/095091 A2 | 8/2007 |
| WO | 2007/134241 A2 | 11/2007 |
| WO | 2009/023311 A2 | 2/2009 |
| WO | 2009/137436 A2 | 11/2009 |

OTHER PUBLICATIONS

FDA Guidance (Waiver of In Vivo Bioavailability and Bioequivalence Studies for Immediate-Release Solid Oral Dosage Forms Based on a Biopharmaceutics Classification System) Dec. 2017.*
Song et al.: "Effect of the six-mer synthetic peptide (AT1002) fragment of zonula occludens toxin on the intestinal absorption of cyclosporin A"; International Journal of Pharmaceutics 351 (2008), pp. 8-14.
Song et al.: "The Impact of AT1002 on the Delivery of Ritonavir in the Presence of Bioadhesive Polymer, Carrageenan"; Arch Pharm Res. vol. 35, No. 5 (2012), pp. 937-943.
Song et al.: "The Influence of Stabilizer and Bioadhesive Polymer on the Permeation-Enhancing Effect of AT1002 in the Nasal Delivery of a Paracellular Marker"; Arch Pharm Res. vol. 35, No. 2 (2012), pp. 359-366.
Goldblum et al.: "The active Zot domain (aa 288-293) increases ZO-1 and myosin 1C serine/threonine phosphorylation, alters interaction between ZO-1 and its binding partners, and induces tight junction disassembly through proteinase activated receptor 2 activation"; The FASEB Journal, Research Communication, vol. 25 (2011), pp. 144-158.
International Search Report for PCT/KR2015/005308, dated Sep. 1, 2015.
Song et al.: "Paracellular permeation-enhancing effect of AT1002 C-terminal amidation in nasal delivery"; Drug Design, Development and Therapy, Dovepress (2015): 9, pp. 1815-1823.
Search Report for European Application No. 15814702.5, dated May 9, 2017.

* cited by examiner

*Primary Examiner* — Julie Ha
(74) *Attorney, Agent, or Firm* — Melissa M. Hayworth; E. Joseph Gess

(57) ABSTRACT

As described herein, an peptide of SEQ ID NO: 1 is modified at the terminal end. Specifically, the carboxyl-group of the leucine at the terminal end of the amino acid sequence FCIGRL (SEQ ID NO: 1) is modified with a —$CONH_2$. This modified peptide is used as a permeation enhancer to boost the mucous membrane permeation, thereby noticeably increasing the bioavailability of a drug that is administered together with the modified peptide. The drug to be administered with the modified peptide can be cyclosporine A.

18 Claims, 1 Drawing Sheet
Specification includes a Sequence Listing.

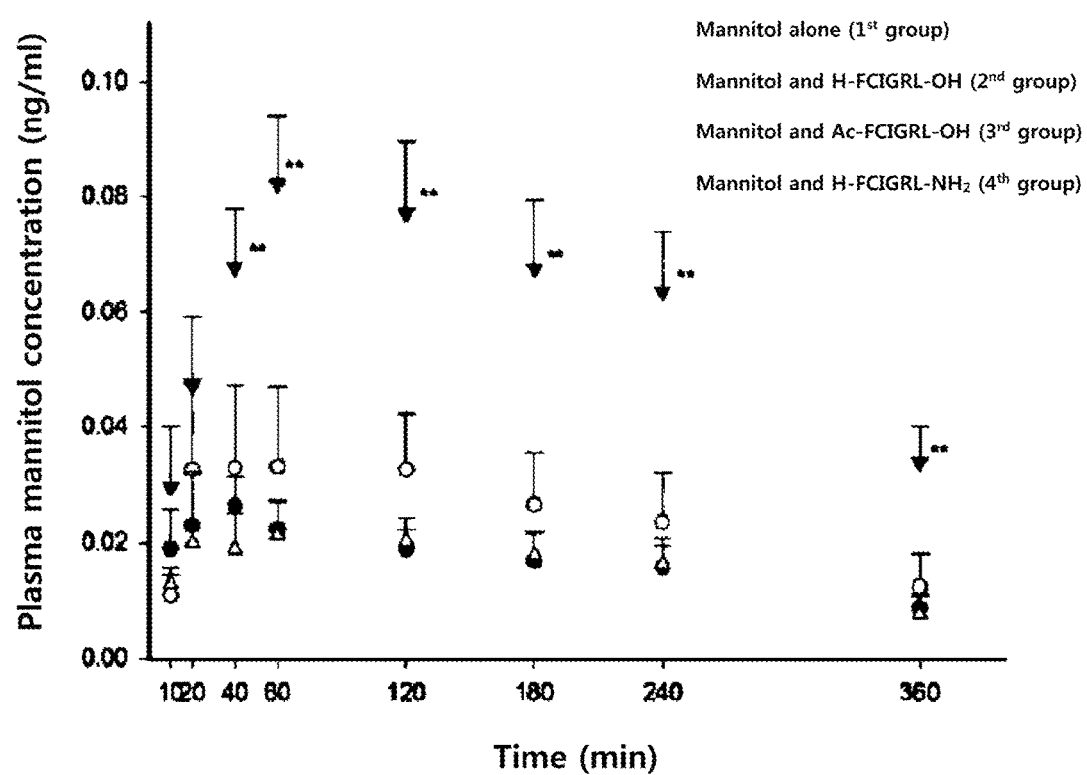

PEPTIDE AS ABSORPTION ENHANCER AND COMPOSITION CONTAINING SAME

This application is a National Stage Application of PCT/KR2015/005308, filed 27 May 2015, which claims benefit of Korean Patent Application No. 10-2014-0080608, filed 30 Jun. 2014, the contents of all of which are hereby incorporated by reference in their entireties.

TECHNICAL FIELD

The present invention relates to a peptide as a permeation enhancer and a composition or preparation comprising the same. More specifically, the present invention modifies the terminal ends of a peptide and enhances the function of the peptide to boost the mucous membrane permeability of a drug.

BACKGROUND ART

The drugs with low bioavailability, when orally administered, do not work even though they are intrinsically endowed with good efficacy. For this reason, many efforts have been made to enhance the bioavailability of the drugs, particularly small intestinal or nasal mucous membrane permeability when the drugs are administered by oral or nasal route.

Boosting the mucous membrane permeation of drugs with a permeation enhancer can be taken into consideration, where the permeation enhancer promotes the transfer of drugs passing through the paracellular route, that is, the intercellular space between the mucous membrane cells. Examples of the permeation enhancer include surfactants, or peptides or proteins that affect the tight junctions. Yet, the surfactants are toxic to the cells, and the peptides or proteins are likely to display low physicochemical stability depending on the pH value of the administered drugs or the absorbing areas due to their structural properties. The use of the surfactants is thus very limited. The peptides or proteins that affect the tight junctions are almost nontoxic to the cells, yet they are required to go with adjuvants or additives like carrageenan, remaining the problem in association with the preparation and reactivity with the administered drugs.

It is therefore necessary to develop a method and substance as a permeation enhancer that is nontoxic to the cells and capable of affecting the open/close of the tight junctions and enhancing the permeation of drugs without the aid of an adjuvant or an additive.

PRIOR ART DOCUMENTS

Patent Documents

Patent Document 1: WO 07/095091
Patent Document 2: WO 07/134241

Non-Patent Documents

Non-Patent Document 1: International Journal of Pharmaceutics 351 (2008) 8-14
Non-Patent Document 2: Arch Pharm Res. Vol. 35, No. 5, 937-943, 2012
Non-Patent Document 3: Arch Pharm Res. Vol. 35, No. 2, 359-366, 2012

DISCLOSURE OF INVENTION

Technical Problem

It is therefore an object of the present invention to provide a peptide as a permeation enhancer that helps the permeation of active components of drugs into the body.

It is another object of the present invention to provide a composition for enhancing the permeation of active components, which composition contains a peptide as a permeation enhancer.

It is still another object of the present invention to provide a preparation for enhancing the permeation of active components, which preparation contains a peptide as a permeation enhancer.

Technical Solution

The present invention provides a peptide having an amino acid sequence represented by the following sequence number 1 (SEQ ID NO:1) or an amino acid sequence homologous to the sequence number 1 (SEQ ID NO:1) so that the carboxyl group (—COOH) of Leucine at the terminal end of the amino acid sequence is changed into —CONH$_2$.

Sequence Number 1 (SEQ ID NO: 1): Phe-Cys-Ile-Gly-Arg-Leu (FCIGRL)

The peptide of the present invention may have the function of a permeation enhancer through mucous membranes. The peptide of the present invention can serve as a permeation enhancer with the enhanced function to remarkably boost the mucous membrane permeation by changing the carboxyl group (—COOH) of the peptide having an amino acid sequence of the sequence number 1 (SEQ ID NO:1) or an amino acid sequence homologous to the sequence number 1 (SEQ ID NO:1) into —CONH$_2$. Hence, administering the peptide of the present invention together with an active component like a drug can boost the permeation of the drug through mucous membranes without the aid of an adjuvant such as a peptide stabilizer or an additive and thus enhance the bioavailability of the active component.

In the prior art document (Arch Pharm Res. Vol. 35, No. 2, 359-366, 2012), the peptide of the sequence number 1 (SEQ ID NO:1) cannot maintain the intact form of peptide over time in a buffer solution that is slightly acid (pH 5.0), neutral, and basic, which fact explicitly shows that the peptide of the sequence number 1 (SEQ ID NO:1) has a deterioration in the function of boosting the permeation of the active component under the environment that ranges from slightly acid, neutral or basic. The prior art document suggests solutions to this problem, such as using a mixed solution of amino acids to delay the degradation of the peptide and administering the peptide of the sequence number 1 (SEQ ID NO:1) in combination with a mucous membrane adhesive agent like carrageenan.

The peptide of the present invention, which is either a peptide having the sequence number 1 (SEQ ID NO:1) or a modified peptide homologous to the sequence number 1 (SEQ ID NO:1), can remarkably enhance the permeation of active components such as drugs without the aid of an adjuvant and thus effectively act as a mucous membrane permeation enhancer.

Particularly, the terminal-modified peptide of the present invention opens the tight junction that is the space between two adjacent cells to allow the drugs to pass through the intercellular space, so the drugs with low bioavailability can easily permeate mucous membranes, specifically of small intestine, nasal cavity, oral cavity, skin, lung, vagina, rectum, or large intestine, thereby enhancing the bioavailability of the drugs with ease.

The peptide of the present invention may also enhance the nasal mucous membrane permeation of a paracellular marker, mannitol, which is used to monitor the paracellular permeation of a drug. Mannitol can be used as a paracellular drug permeation marker of paracellular route, because it nearly cannot pass through the mucous membranes in the tight junction between normal cell membranes. When the use of a permeation enhancer results in the increased permeability of mannitol through the mucous membrane, it explicitly shows that the permeation enhancer, if not cytotoxic, can display its high efficacy by opening the tight junction between two adjacent cells to enhance the permeation of mannitol.

The peptide of the present invention remarkably promotes the permeation of mannitol through the nasal mucous membrane in relation to the peptide of the sequence number 1 (SEQ ID NO:1) in which the terminal end of the sequence is not modified. This shows that the modified peptide of the present invention opens the tight junction between the mucous membrane cells, only to greatly increase the paracellular route permeation of a drug.

The sequence number 1 of the present invention has an amino acid sequence of FCIGRL (SEQ ID NO:1), that is, Phe-Cys-Ile-Gly-Arg-Leu.

In the present invention, the amino acid is an organic compound containing an amino group and a carboxyl group. The peptide contains at least two amino acids.

In the present invention, the amino acid sequence of the peptide has the left-to-right directionality that is the normal direction from amino-terminal end to carboxyl-terminal end. In the amino acid sequence of the peptide, the left-sided terminal end may contain —$NH_2$ that is an amino group present in the amino acid terminal, whereas the right-sided terminal end may contain —COOH that is a carboxyl group present in the amino acid terminal.

In the notation method for the amino acid sequence, —$NH_2$ and —COOH may not be shown in the left and right terminal ends of the amino acid sequence, respectively. Otherwise, when —$NH_2$ and —COOH are shown in the left and right terminal ends of the amino acid sequence, respectively, it means that —$NH_2$ and —COOH are located at the terminals of each amino acid contained in the amino acid sequence. In other words, the sequence number 1 is FCIGRL, that is, Phe-Cys-Ile-Gly-Arg-Leu, representing an unmodified amino acid sequence, which can also be denoted as $NH_2$— FCIGRL-COOH or H-FCIGRL-OH.

In the present invention, the amino acid sequence that is homologous to the amino acid sequence of the sequence number 1 may mean a sequence in which one amino acid of the sequence number 1 is substituted. In the present invention, the amino acid sequence homologous to the sequence number 1 may be any one of sequence numbers 2 to 6. For example, the amino acid sequence homologous to the sequence number 1 may be as follows:

Sequence number 2 (SEQ ID NO: 2): $Xaa_1$-Cys-Ile-Gly-Arg-Leu ($X_1$CIGRL)

Sequence number 3 (SEQ ID NO: 3): Phe-$Xaa_2$-Ile-Gly-Arg-Leu ($FX_2IGRL$)

Sequence number 4 (SEQ ID NO: 4): Phe-Cys-$Xaa_3$-Gly-Arg-Leu ($FCX_3GRL$)

Sequence number 5 (SEQ ID NO: 5): Phe-Cys-Ile-$Xaa_4$-Arg-Leu ($FCIX_4RL$)

Sequence number 6 (SEQ ID NO: 6): Phe-Cys-Ile-Gly-$Xaa_5$-Leu ($FCIGX_5L$)

In the sequence number 2, $Xaa_1$, that is, $X_1$ may be Ala, Val, Leu, Ile, Pro, Trp, or Met. In the sequence number 3, $Xaa_2$, that is, $X_2$ may be Gly, Ser, Thr, Tyr, Asn, or Gln. In the sequence number 4, $Xaa_3$, that is, $X_3$ may be Ala, Val, Leu, Pro, Trp, or Met. In the sequence number 5, $Xaa_4$, that is, $X_4$ may be Ser, Thr, Tyr, Asn, Ala, or Gln. In the sequence number 6, $Xaa_5$, that is, $X_5$ may be Lys or His.

In the present invention, when —H of the left-sided amino-terminal end of the amino acid sequence or —OH of the right-sided carboxyl-terminal end is substituted by X, NHX or X may appear at the left terminal end of the amino acid sequence; or COX or X may be shown at the right terminal end of the amino acid sequence. For example, when H of the —$NH_2$ present in the phenyl alanine on the left side of the sequence number 1 is substituted by an acetyl group (—C(=O)—$CH_3$, Ac), the amino acid sequence can be expressed as AcNH-FCIGRL or Ac-FCIGRL. When OH of the —COOH in the leucine on the right side of the sequence number 1 is substituted by $NH_2$, then the amino acid sequence can be denoted as FCIGRL-$CONH_2$ or FCIGRL-$NH_2$. When H of the —$NH_2$ present in the phenyl alanine on the left side of the sequence number 1 is substituted by an acetyl group and OH of the —COOH present in the leucine on the right side of the sequence number 1 is substituted by the —$NH_2$, the amino acid sequence can be denoted as NHAc-FCIGRL-$CONH_2$ or Ac-FCIGRL-$NH_2$. The same rule is applied to the sequence numbers 2 to 6.

The present invention provides a composition for enhancing mucous membrane permeability that comprises a peptide having an amino acid sequence of SEQ ID NO:1 or an amino acid sequence homologous to the sequence number 1, where the carboxyl group (—COOH) of Leucine at the terminal end of the amino acid sequence is modified into —$CONH_2$.

In the composition of the present invention, the peptide opens the tight junction present in the cell membranes to enhance the mucous membrane permeation of an active substance like a drug, etc.

In the present invention, the mucous membrane as used herein refers to a soft tissue that constitutes the inner wall of the respiratory organs, digestive organs and generative organs that are in direct contact with outside and plays a part in the function related to the penetration and secretion of substances. In the present invention, the mucous membrane as used herein is not specifically limited in terms of the type and may be a mucous membrane with tight junctions. The mucous membrane is preferably a mucous membrane of oral cavity, nasal cavity, small intestine, large intestine, rectum, vagina, lungs, skin, etc., more preferably, a small intestinal mucous membrane or a nasal mucous membrane.

In the present invention, the composition for enhancing mucous membrane permeability may further comprise an active component like a drug, etc. When administered together with an active component, the peptide of the present invention opens the tight junctions present in the mucous membranes and thus allows the active component to pass through the mucous membranes, thereby enhancing the permeation of the active component. In the case of an oral administration of the peptide and the active component at the same time, for example, the peptide opens the tight junction present in the mucous membrane of the small intestine, allowing the active component to pass through the mucous membrane of the small intestine, thereby to promote the penetration of the active component. This leads to the remarkably enhanced bioavailability of the active component. Accordingly, administration of the active component having a low bioavailability together with the peptide noticeably enhances the efficacies of the active component.

In the present invention, the active component as used herein is not specifically limited in terms of the type and may be any substance of which the bioavailability needs to be enhanced. The active component may be anticancer drugs, antibiotics, anti-inflammatory drugs, pain relievers, immunosuppressive drugs, peptides, hormones, or a mixture thereof.

For example, the active component may include insulin, paclitaxel, acyclovir, cyclosporine A, doxorubicin, ritonavir, saquinavir, aspirin, retinoid, methotrexate, tamoxifen or its pharmaceutically acceptable salts, dexamethasone or its pharmaceutically acceptable salts, trapidol, angiopeptin, dopamine, bromocriptine or its pharmaceutically acceptable salt, pergolide or its pharmaceutically acceptable salts, captopril, enalapril, ascorbic acid, alpha-tocopherol, deferoxamine, AZT, famciclovir, 5-aminolevulinic acid, prednisone, methylprednisone, thalidomide, rifamycin and its derivatives, busulfan, melphalan, fluorourasil, carmustine, lomustine, carboplastin, cisplastin, docetaxel, finasteride, dutasteride, vincristine, ticlopidine, vinblastine, bleomycin, pentostatin, gemcitabine, thioguanine, colchicine, cytochalacin, deoxyribonucleic acid, oseltamivir, amantadine, rimantadine or its pharmaceutically acceptable salts, meloxicam, lornoxicam, indomethacin, ketorolac, betamethasone, or mixtures thereof.

Preferably, the active component may be insulin, paclitaxel, acyclovir, cyclosporine A, doxorubicin, ritonavir, saquinavir, or a mixture thereof.

Further, the active component may be a drug belonging to the Class III or Class IV of the biopharmaceutics classification system (BCS).

In the present invention, the amino acid sequence homologous to the amino acid sequence of the sequence number 1 may mean a sequence in which one amino acid of the sequence number 1 is substituted. In the present invention, the amino acid sequence homologous to the sequence number 1 may be any one of the sequence numbers 2 to 6.

In the present invention, the content of the peptide contained in the composition is not specifically limited as long as it does not restrain the effects of the peptide. The composition may contain 0.001 to 50 wt. % of the peptide.

In the present invention, the route and frequency of administration of the composition may be appropriately regulated depending on the type of the active component, the health condition of the patient, and the severity of the disease.

In the present invention, the composition may be taken by several routes of administration, such as, oral route, nasal route, buccal route, transdermal route, transpulmorary route, rectal route, or vaginal route.

In the present invention, the composition may be administered once a day or multiple times a day.

In the present invention, the dosage of the composition may be appropriately adjusted depending on the condition (e.g., age, weight, sex, etc.) of the patient, the type and severity of the disease, and the type of the active component. For example, the composition may be administered to take the peptide in an amount of 0.0001 mg/kg to 100 mg/kg.

In the present invention, the composition may further comprise a protease inhibitor, that is, proteolytic enzyme inhibitor. The protease inhibitor as used herein is not specifically limited in terms of the type as long as it does not restrain the effects of the composition. For example, the protease inhibitor may be bestatin, L-trans-3-carboxyoxirane-2-carbonyl-L-leucine agmatine, ethylenediaminetetraacetic acid, phenylmethylsulfonyl fluoride, aprotinin, amyloid protein precursor, amyloid beta precursor protein, alpha1-propinase inhibitor, collagen VI, bovine pancreatic trypsin inhibitor (BPTI), 4-(2-aminoethyl)-benzenesulfonyl fluoride, antipine, antipyn, benzamidine, chymostatin, ε-aminocarproate, N-ethylmaleimide, leupeptin, pepstatin A, phosphoamidon, or a mixture thereof.

In the present invention, the composition may further comprise a pharmaceutically acceptable adjuvant or additive. The adjuvant or additive may include saline solution, sterile water, Ringer's solution, buffered saline, dextrose solution, maltodextrin solution, glycerol, ethanol, amino acid, or a mixture of at least one thereof. Under necessity, the composition may further include another additives commonly used, such as a stabilizer, a mucous membrane adhesive agent, an antioxidant, a buffer solution, a bacteriostat, etc. Also, a diluent, a dispersing agent, a surfactant, a coupling agent, or a lubricant may be further added to manufacture the composition into a preparation in the dosage form of a liquid, such as an aqueous solution, a suspension, an emulsion, etc., pills, capsules, granules, or tablets.

The present invention provides a preparation comprising: a peptide having an amino acid sequence of the sequence number 1 or an amino acid sequence homologous to the sequence number 1, where the carboxyl group (—COOH) of Leucine at the terminal end of the amino acid sequence is modified into —$CONH_2$; and an active component such as a drug, etc.

The preparation of the present invention, containing the peptide, remarkably enhances the bioavailability of the active component. As described above, the peptide opens the tight junction present in the mucous membranes to promote the permeation of the active component, thereby maximizing the therapeutic effects of the active component.

The preparation of the present invention may further comprise a protease inhibitor, that is, a proteolytic enzyme inhibitor. The protease inhibitor as used herein is not specifically limited in terms of the type as long as it does not restrain the effects of the preparation.

The preparation of the present invention may further comprise a pharmaceutically acceptable adjuvant or additive in addition to the peptide and the active component. The pharmaceutically acceptable adjuvant or additive as used herein is not specifically limited in terms of the type as long as it does not restrain the effects of the peptide and the active component, so it may be any known pharmaceutically acceptable additive.

In the present invention, the pharmaceutically acceptable adjuvant or additive may be appropriately selected depending on the route of administration of the preparation. For example, the preparation, designed for oral administration, may go with a pharmaceutically acceptable additive in order to prevent a degradation of the peptide.

In the present invention, the pharmaceutically acceptable adjuvant or additive or additive may include saline solution, sterile water, Ringer's solution, buffered saline, dextrose solution, maltodextrin solution, glycerol, ethanol, amino acid, or a mixture of at least one thereof. Under necessity, the composition may further include another general additive, such as a stabilizer, a mucous membrane adhesive agent, an antioxidant, a buffer solution, a bacteriostat, etc. Also, a diluent, a dispersing agent, a surfactant, a coupling agent, or a lubricant may be further added to manufacture the composition into a preparation in the dosage form of a liquid, such as an aqueous solution, a suspension, an emulsion, etc., pills, capsules, granules, or tablets. Accordingly, the composition of the present invention may come in patches, a liquid, pills, capsules, granules, tablets, suppositories, or the like. These preparations may be prepared by the general methods used for formulation in the art or by the methods disclosed in the Remington's Pharmaceutical Science (18th edition), Mack Publishing Company, Easton Pa. The composition of the present invention may come in different preparations depending on the disease or the components.

The preparation of the present invention may be taken by oral, nasal, buccal, transdermal, transpulmonary, rectal, or vaginal administration. For a specific route of administration, the preparation of the present invention may be formulated into an appropriate dosage form.

In the present invention, the amino acid sequence of the sequence number 1 and the amino acid sequence homologous to the sequence number 1 may mean a sequence in which one amino acid of the sequence number 1 is substituted. In the present invention, the amino acid sequence homologous to the sequence number 1 may be any one of the sequence numbers 2 to 6.

In the present invention, the active component contained in the preparation is not specifically limited in terms of the type. The active component is preferably a substance in need of the higher bioavailability and its type is given as listed above.

The present invention provides a method for administering a peptide into an animal including human, preferably a mammal including human, where the peptide has an amino acid sequence represented by the sequence number 1 (SEQ ID NO:1) or an amino acid sequence homologous to the sequence number 1 (SEQ ID NO:1) so that the carboxyl group (—COOH) of Leucine at the terminal end of the amino acid sequence is modified into —CONH$_2$. The peptide may be administered together with an active component to boost the mucous membrane permeation of the active component.

The present invention also provides a usage of a peptide for enhancement of mucous membrane permeation, where the peptide has an amino acid sequence represented by the sequence number 1 (SEQ ID NO:1) or an amino acid sequence homologous to the sequence number 1 (SEQ ID NO:1) so that the carboxyl group (—COOH) of Leucine at the terminal end of the amino acid sequence is changed into —CONH$_2$.

Advantageous Effect

The peptide of the present invention is used as a permeation enhancer to boost the permeation of an active component such as a drug, which is administered together with the peptide, thereby remarkably enhancing the bioavailability of the active component. As a result, it is possible to greatly enhance the therapeutic effects of the active component.

BRIEF DESCRIPTION OF DRAWINGS

FIG. 1 is a concentration-time graph showing the nasal membrane permeability of mannitol in the presence of the peptide of the present invention, a peptide unmodified at the terminal ends, or a peptide modified at the other terminal ends.

MODE FOR INVENTION

Hereinafter, the disclosure of the present invention will be described in further detail with reference to examples, which are given for the understanding of the disclosure of the present invention and not intended to limit the scope of the claims in the present invention. The examples of the present invention are provided for those skilled in the related art of the present invention to completely understand the present invention.

As for the substances used in the present invention, if not specified otherwise, the reagents used in the preparation of the peptide are available from AnaSpec (Fremont, Calif., USA), and the reagents used in the preparation of the composition and the preparation are available from Sigma-Aldrich (St. Louis, Mo., USA).

Preparation Example 1

Preparation of FCIGRL

FGIGRL was synthesized by the Fmoc solid phase peptide synthesis (SPPS) method to perform a coupling one by one from the carboxyl-terminal end, as follows.

(1) An NH$_2$-Leu-2-chloro-trityl resin in which leucine was attached to a resin was provided.

(2) In all the amino acid materials used in the synthesis of peptide, the amino-terminal end was protected with Fmoc, and the residues were protected with Trt, Boc, t-Bu, etc., all of which were removed from an acid, trifluoroacetic acid (TFA), as denoted by Fmoc-Phe-OH, Fmoc-Cys(Trt)-OH, Fmoc-Ile-OH, Fmoc-Gly-OH, Fmoc-Arg(Pbf)-OH, and so on.

(3) A solution of a protected amino acid and a coupling reagent(HBTU/HOBt/NMM (HBTU=2-(1H-benzotriazole-1-yl)-1,1,3,3-tetramethylaminium hexafluorophosphate; HOBt=N-hydroxybenzotriazole; NMM=4-methylmorpholine) in DMF was added to the NH$_2$-Leu-2-chloro-trityl resin to activate a 2-hour coupling reaction. After the completion of the reaction, the resin was rinsed with DMF, MeOH and DMF in sequential order.

(4) For removal of the Fmoc, 20% piperidine dissolved in DMF was added to perform two cycles of the reaction for 5 minutes at the room temperature. After the completion of the reaction, the resin was rinsed with DMF, MeOH and DMF in sequential order.

(5) The above stepwise reactions were repeatedly performed to form a peptide framework (NH$_2$-Phe-Cys-Ile-Gly-Arg-Leu-2-chloro-Trityl Resin). Then, a cleavage cocktail (TFA/EDT/Thioanisole/TIS/H$_2$O=90/2.5/2.5/2.5/2.5) (TFA=trifluoroacetic acid; EDT=1,2-ethanedithiol; TIS=triisopropylsilane) was added to remove the protective groups from the peptide residues and separate the peptide from the resin.

(6) Cooling diethyl ether, 10-fold volume of the peptide, was added to the separated peptide of the step (5) to precipitate the peptide. The peptide precipitate was subjected to centrifugal separation at 3,000 rpm for 10 minutes. The resultant filtrate was discarded, and cooling diethyl ether was added two more times. Another centrifugal separation was performed to yield a peptide, which was purified with Prep-HPLC and then freeze-dried.

Preparation Example 2

Preparation of Ac-FCIGRL

A modified peptide was prepared, where H of the amine group (—NH$_2$) at the amino-terminal end of FCIGRL was substituted by an acetyl group. In the preparation method, the steps (1) to (4) are the same as the steps (1) to (4) of the synthesis method in the Preparation Example 1, and the subsequent steps are as follows.

(5) The above stepwise reactions were repeatedly performed to form a peptide framework (NH$_2$-Phe-Cys-Ile-Gly-Arg-Leu-2-chloro-Trityl Resin). Then, a solution of acetic anhydride and DIPEA in DMF was added to activate a reaction for 30 minutes. After the completion of the reaction, the resin was rinsed with DMF, MeOH and DMF in sequential order.

(6) A cleavage cocktail (TFA/EDT/Thioanisole/TIS/H$_2$O=90/2.5/2.5/2.5/2.5) was added to the peptide framework synthesized in the step (5) to remove the protective groups from the peptide residues and separate the peptide from the resin.

(7) Cooling diethyl ether, 10-fold volume of the peptide, was added to the separated peptide of the step (5) to precipitate the peptide. The peptide precipitate was subjected to centrifugal separation at 3,000 rpm for 10 minutes. The resultant filtrate was discarded, and cooling diethyl ether was added two more times. Another centrifugal separation was performed to yield a peptide, which was purified with Prep-HPLC and then freeze-dried.

Preparation Example 3

Preparation of Ac-FCIGRL-NH$_2$

The modified peptide was prepared such that H of the amine group (—NH$_2$) present in the amino-terminal end of FGIGRL was substituted with an acetyl group and —OH of the carboxyl group (—COOH) was substituted with —NH$_2$. The preparation method was carried out as follows.

(1) An NH$_2$-Leu-MBHA link amide Resin in which leucine was attached to a resin was provided.

(2) In all the amino acid materials used in the synthesis of peptide, the amino-terminal end was protected with Fmoc, and the residues were protected with Trt, Boc, t-Bu, etc., all of which were removed from an acid, trifluoroacetic acid (TFA), as denoted by Fmoc-Phe-OH, Fmoc-Cys(Trt)-OH, Fmoc-Ile-OH, Fmoc-Gly-OH, Fmoc-Arg(Pbf)-OH, and so on.

(3) A solution of a protected amino acid and a coupling reagent(HBTU/HOBt/NMM) in DMF was added to the provided NH$_2$-Leu-MBHA link amide resin to activate a 2-hour coupling reaction. After the completion of the reaction, the resin was rinsed with DMF, MeOH and DMF in sequential order.

(4) For removal of the Fmoc, 20% piperidine dissolved in DMF was added to perform two cycles of the reaction for 5 minutes at the room temperature. After the completion of the reaction, the resin was rinsed with DMF, MeOH and DMF in sequential order.

(5) The above stepwise reactions were repeatedly performed to form a peptide framework (NH$_2$-Phe-Cys-Ile-Gly-Arg-Leu-MBHA link amide Resin). Then, a solution of acetic anhydride and DIPEA in DMF was added to activate a reaction for 30 minutes. After the completion of the reaction, the resin was rinsed with DMF, MeOH and DMF in sequential order.

(6) A cleavage cocktail (TFA/EDT/Thioanisole/TIS/H$_2$O=90/2.5/2.5/2.5/2.5) was added to the peptide framework (NH$_2$-Phe-Cys-Ile-Gly-Arg-Leu-MBHA link amide Resin) synthesized in the step (5) to remove the protective groups from the peptide residues and separate the peptide from the resin.

(7) Cooling diethyl ether, 10-fold volume of the peptide, was added to the separated peptide of the step (6) to precipitate the peptide. The peptide precipitate was subjected to centrifugal separation at 3,000 rpm for 10 minutes. The resultant filtrate was discarded, and cooling diethyl ether was added two more times. Another centrifugal separation was performed to yield a peptide, which was purified with Prep-HPLC and then freeze-dried.

Example 1

Synthesis of FCIGRL-NH$_2$

The modified peptide was prepared such that —OH of the carboxyl group (—COOH) of FGIGRL was substituted with —NH$_2$. The preparation method was carried out as follows.

(1) An NH$_2$-Leu-MBHA link amide resin in which leucine was attached to a resin was provided.

(2) In all the amino acid materials used in the synthesis of peptide, the amino-terminal end was protected with Fmoc, and the residues were protected with Trt, Boc, t-Bu, etc., all of which were removed from an acid, trifluoroacetic acid (TFA), as denoted by Fmoc-Phe-OH, Fmoc-Cys(Trt)-OH, Fmoc-Ile-OH, Fmoc-Gly-OH, Fmoc-Arg(Pbf)-OH, and so on.

(3) A solution of a protected amino acid and a coupling reagent, HBTU/HOBt/NMM, in DMF was added to the provided NH$_2$-Leu-MBHA link amide resin to activate a 2-hour coupling reaction. After the completion of the reaction, the resin was rinsed with DMF, MeOH and DMF in sequential order.

(4) For removal of the Fmoc, 20% piperidine dissolved in DMF was added to perform two cycles of the reaction for 5 minutes at the room temperature. After the completion of the reaction, the resin was rinsed with DMF, MeOH and DMF in sequential order.

(5) The above stepwise reactions were repeatedly performed to form a peptide framework (NH$_2$-Phe-Cys-Ile-Gly-Arg-Leu-MBHA link amide Resin). Then, a cleavage cocktail (TFA/EDT/Thioanisole/TIS/H$_2$O=90/2.5/2.5/2.5/2.5) was added to the peptide framework (NH$_2$-Phe-Cys-Ile-Gly-Arg-Leu-MBHA link amide Resin) to remove the protective groups from the peptide residues and separate the peptide from the resin.

(6) Cooling diethyl ether, 10-fold volume of the peptide, was added to the separated peptide of the step (5) to precipitate the peptide. The peptide precipitate was subjected to centrifugal separation at 3,000 rpm for 10 minutes. The resultant filtrate was discarded, and cooling diethyl ether was added two more times. Another centrifugal separation was performed to yield a peptide, which was purified with Prep-HPLC and then freeze-dried.

Example 2

Evaluation on Effect of FCIGRL-NH$_2$ to Enhance Mucous Membrane Permeability 1. Lab Animal Male SD (Sprague-Dawley) rats (280-300 g) were provided to adapt to each separate cage of the animal facility at least 2 days. At this point, foods and water were freely allowed to the rats, which were exposed to light for 12 hours and kept in dark for another 12 hours. One day before the testing, the rats were provided with water only and kept from eating food.

2. Preparation of Test Substances

The peptides of the Preparation Examples or the Example, and mannitol($^3$H-Mannitol, 14.2 Ci/mmol, PerkinElmer) were used to prepare the individual preparation groups given as follows:

The first preparation group was a control group and prepared as an aqueous solution of 5% (w/v) dextrose containing mannitol without a peptide.

The second preparation group was prepared as an aqueous solution of 5% (w/v) dextrose containing mannitol and the FCIGRL peptide of the Preparation Example 1.

The third preparation group was prepared as an aqueous solution of 5% (w/v) dextrose containing mannitol and the Ac-FCIGRL peptide of the Preparation Example 2.

The fourth preparation group was prepared as an aqueous solution of 5% (w/v) dextrose containing mannitol and the FCIGRL-NH$_2$ peptide of the Example 1.

But, the preparation group containing Ac-FCIGRL-NH$_2$ peptide of the Preparation Example 3 and mannitol is excluded in the administration testing, because the preparation group containing mannitol and the Ac-FCIGRL-NH$_2$ of the Preparation Example 3 had such a low solubility of the peptide as to make nasal administration of the peptide impossible.

3. Administration of Preparation Groups

The male SD rats provided above 1. were divided into four groups, each having five male SD rats. The first to fourth preparation groups were nasally administered into the first to fourth rat groups, respectively.

At this point, the dosage of each solution was 70 μl per rat, where the dosages of mannitol and each peptide were 20 μCi/kg and 2.5 mg/kg, respectively.

Prior to the nasal administration, each rat was anesthetized to implant a cannula into the jugular vein of it. The solution was taken into the nostrils of the rat through a micropipette (Eppendorf) with caution as not to affect the nasal mucous membrane, while the rat was lying on the back to rest its head sideways against the wall.

4. Measurement of Mannitol Concentration

250 μl of blood was collected from each rat in 10, 20, 40, 60, 120, 180, 240 and 360 minutes after administration of the solution through jugular vein cannulation. The blood was subjected to centrifugal separation at 13,000 rpm for 10 minutes to obtain 100 μl of plasma. A scintillation cocktail solution was added to the plasma. Then, an LS6500 Universal counter (Beckman Coulter, Brea, Calif., USA) was used to measure the radiation quantity for the quantitative analysis of mannitol.

The mannitol concentration in blood from the rats of each group is graphed in FIG. 1. Table 1 presents the pharmacokinetic parameters, that is, AUC, $C_{max}$, $T_{max}$, and $T_{1/2}$ of mannitol.

TABLE 1

| | AUC$_{0-360\ min}$ (min/ng/ml) | $C_{max}$ (pg/ml) | $T_{max}$ (min) | $T_{1/2}$ (min) |
|---|---|---|---|---|
| Mannitol alone (1$^{st}$ group) | 6.08 ± 1.33 | 30.58 ± 6.02 | 35.00 ± 9.57 | 215.45 ± 3.09 |
| Mannitol + FCIGRL (2$^{nd}$ group) | 9.02 ± 3.31 | 38.30 ± 12.48 | 60.00 ± 30.55 | 161.66 ± 33.52 |
| Mannitol + Ac-FCIGRL (3$^{rd}$ group) | 5.87 ± 1.59 | 22.63 ± 5.72 | 66.67 ± 29.06 | 176.48 ± 49.29 |
| Mannitol + FCIGRL-NH$_2$ (4$^{th}$ group) | 22.08 ± 3.54** | 82.06 ± 12.10** | 60.00 ± 0.00* | 177.01 ± 24.18 |

(Note:
with respect to the mannitol-alone administration group (1$^{st}$ group),
*p < 0.05,
**p < 0.01)

As can be seen from Table 1 and FIG. 1, the administration group of mannitol alone, the administration group of mannitol and the peptide of Preparation Example 1, and the administration group of mannitol and the peptide of Preparation Example 2 had no significant difference in the blood mannitol concentration. But, the group taking mannitol and the peptide of Example 1 showed a significant (p<0.01) increase in AUC$_{0-360min}$ and $C_{max}$ of mannitol, which were 3.63 times and 2.68 times higher than those of the administration group of mannitol alone, respectively.

In conclusion, compared with the peptide of H-FCIGRL-OH and the peptides with the acetylated amino-terminal ends, such as Ac-FCIGRL-OH or Ac-FCIGRL-NH$_2$, the modified peptide of the present invention (H-FCIGRL-NH$_2$) in which the carboxyl group (—COOH) of FGIGRL was substituted by NH$_2$ showed a noticeable increase in the permeability of mannitol used as an index substance for drug permeation by opening the tight junctions of the nasal mucous membrane, thereby boosting the mucous membrane permeation of other active substances to enhance the bioavailability of the active substances.

The invention claimed is:

1. A composition for enhancing mucous membrane permeability, the composition comprising an amino acid sequence FCIGRL (SEQ ID NO:1), wherein the carboxyl group (—COOH) of Leucine at the terminal end of the amino acid sequence is modified into —CONH$_2$; and
   an active component, wherein the active component is not linked to the peptide.

2. The composition for enhancing mucous membrane permeability of claim 1, wherein the active component is cyclosporine A.

3. The composition for enhancing mucous membrane permeability of claim 2, wherein the composition further comprises a pharmaceutically acceptable additive or adjuvant.

4. The composition for enhancing membrane permeability of claim 1, wherein the mucous membrane is a mucous membrane with the expressed tight junction.

5. The composition for enhancing membrane permeability of claim 4, wherein the mucous membrane is a mucous membrane of small intestine, nasal cavity, oral cavity, skin, lung, vagina, rectum, or large intestine.

6. A preparation comprising:
   a peptide having an amino acid sequence FCIGRL (SEQ ID NO:1), wherein the carboxyl group (—COOH) of Leucine at the terminal of the amino acid sequence is modified into —CONH$_2$; and
   an active component, wherein the active component is cyclosporine A and is not linked to the peptide.

7. The preparation of claim 6, wherein the preparation is taken by oral, nasal, buccal, transdermal, transpulmorary, rectal, or vaginal administration.

8. The preparation of claim 6, wherein the preparation further comprises a pharmaceutically acceptable additive or adjuvant.

9. The preparation of claim 6, wherein the preparation is for enhancement of mucous membrane permeability.

10. The preparation of claim 6, wherein the preparation contains 0.001 to 50 wt % of the peptide.

11. A method of enhancing permeation of an active component through mucous membranes in a subject comprising administering to a subject in need thereof an active component and a peptide respectively,
    wherein the peptide has an amino acid sequence FCIGRL (SEQ ID NO:1) wherein the carboxyl group (—COOH) of Leucine at the terminal end of the amino acid sequence is modified into —CONH$_2$ and the peptide boosts the mucous membrane permeation of the active component, and
    the active component is a cyclosporine A and is not linked to the peptide.

12. The method of claim 11, wherein the mucous membrane is selected from a group consisting of a mucous membrane of small intestine, a mucous membrane of nasal cavity, a mucous membrane of oral cavity, a mucous membrane of skin, a mucous membrane of lung, a mucous membrane of vagina, a mucous membrane of rectum, and a mucous membrane of large intestine.

13. The method of claim 12, wherein the active component and peptide are in the form of a dosage form selected from the group consisting of a liquid, capsules, granules and tablets.

14. The method of claim 13, wherein the liquid dosage form is selected from the group consisting of an aqueous solution, suspension, and an emulsion.

15. The method of claim 11, wherein the peptide opens a tight junction between adjacent cells in the mucous membrane.

16. The method of claim 11, wherein the active component and the peptide are administered once a day or multiple times a day.

17. The method of claim 11, wherein the peptide is administered in an amount of 0.0001 mg/kg to 100 mg/kg.

18. The method of claim 13, wherein the dosage form further comprises a pharmaceutically acceptable additive or adjuvant.

* * * * *

SEQUENCE LISTING

```
<160> NUMBER OF SEQ ID NOS: 6

<210> SEQ ID NO 1
<211> LENGTH: 6
<212> TYPE: PRT
<213> ORGANISM: Artificial Sequence
<220> FEATURE:
<223> OTHER INFORMATION: synthetic peptide

<400> SEQUENCE: 1

Phe Cys Ile Gly Arg Leu
1               5

<210> SEQ ID NO 2
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: PEPTIDE
<222> LOCATION: (1)
<223> OTHER INFORMATION: Xaa can be Ala Val Leu Ile Pro Trp Tyr or Met

<400> SEQUENCE: 2

Xaa Cys Ile Gly Arg Leu
1               5

<210> SEQ ID NO 3
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: PEPTIDE
<222> LOCATION: (2)
<223> OTHER INFORMATION: Xaa can be Gly Ser Thr Tyr Asn or Gln

<400> SEQUENCE: 3

Phe Xaa Ile Gly Arg Leu
1               5

<210> SEQ ID NO 4
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: PEPTIDE
<222> LOCATION: (3)
<223> OTHER INFORMATION: Xaa can be Ala Val Leu Pro Trp or Met

<400> SEQUENCE: 4

Phe Cys Xaa Gly Arg Leu
1               5

<210> SEQ ID NO 5
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: PEPTIDE
<222> LOCATION: (4)
<223> OTHER INFORMATION: Xaa can be Ser Thr Tyr Asn Ala or Gln

<400> SEQUENCE: 5
```

```
Phe Cys Ile Xaa Arg Leu
1               5

<210> SEQ ID NO 6
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: PEPTIDE
<222> LOCATION: (5)
<223> OTHER INFORMATION: Xaa can be Lys or His

<400> SEQUENCE: 6

Phe Cys Ile Gly Xaa Leu
1               5
```